US00PP23942P2

(12) United States Plant Patent
Smaal

(10) Patent No.: US PP23,942 P2
(45) Date of Patent: Oct. 1, 2013

(54) POINSETTIA PLANT NAMED 'BKPONCH'

(50) Latin Name: ***Euphorbia pulcherrima* Willd.**
Varietal Denomination: BKPONCH

(75) Inventor: Andreas Smaal, De Kwakel (NL)

(73) Assignee: Agriom B.V., De Kwakel (NL)

( * ) Notice: Subject to any disclaimer, the term of this patent is extended or adjusted under 35 U.S.C. 154(b) by 0 days.

(21) Appl. No.: 13/385,288

(22) Filed: Feb. 10, 2012

(51) Int. Cl.
*A01H 5/00* (2006.01)

(52) U.S. Cl.
USPC ..... Plt./307

(58) Field of Classification Search
USPC ..... Plt./307
See application file for complete search history.

*Primary Examiner* — Kent L Bell
(74) *Attorney, Agent, or Firm* — C. A. Whealy

(57) ABSTRACT

A new and distinct cultivar of Poinsettia plant named 'BKPONCH', characterized by its upright plant habit; moderately vigorous growth habit; smooth, flat and horizontal flower bracts; large inflorescences with bright red-colored flower bracts; relatively large cyathia; and excellent post-production longevity.

2 Drawing Sheets

Botanical designation: *Euphorbia pulcherrima* Willd.
Cultivar denomination: 'BKPONCH'.

BACKGROUND OF THE INVENTION

The present invention relates to a new and distinct cultivar of Poinsettia plant, botanically known as *Euphorbia pulcherrima* Willd., and hereinafter referred to by the name 'BKPONCH'.

The new Poinsettia plant is a product of a planned breeding program conducted by the Inventor in De Kwakel, The Netherlands. The objective of the breeding program is to create new freely branching Poinsettia plants that have red-colored flower bracts and good postproduction longevity.

The new Poinsettia plant originated from a cross-pollination made by the Inventor in February, 2007 in De Kwakel, The Netherlands of a proprietary selection of *Euphorbia pulcherrima* Willd. identified as code number 204155-033, not patented, as the female, or seed, parent with a proprietary selection of *Euphorbia pulcherrima* Willd. identified as code number 205265-001, not patented, as the male, or pollen, parent. The new Poinsettia plant was discovered and selected by the Inventor as a single flowering plant within the progeny of the stated cross-pollination in a controlled greenhouse environment in De Kwakel, The Netherlands in March, 2008.

Asexual reproduction of the new Poinsettia plant by terminal vegetative cuttings in a controlled greenhouse environment in De Kwakel, The Netherlands since June, 2009 has shown that the unique features of this new Poinsettia plant are stable and reproduced true to type in successive generations of asexual reproduction.

SUMMARY OF THE INVENTION

Plants of the new Poinsettia have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'BKPONCH'.

These characteristics in combination distinguish 'BKPONCH' as a new and distinct cultivar of Poinsettia plant:

1. Upright plant habit.
2. Moderately vigorous growth habit.
3. Smooth, flat and horizontal flower bracts.
4. Large inflorescences with bright red-colored flower bracts.
5. Relatively large cyathia.
6. Excellent post-production longevity.

Plants of the new Poinsettia can be compared to plants of the female parent selection. Plants of the new Poinsettia differ primarily from plants of the female parent selection in the following characteristics:

1. Flower bracts of plants of the new Poinsettia are smoother than flower bracts of plants of the female parent selection.
2. Flower bracts of plants of the new Poinsettia are horizontal whereas flower bracts of plants of the female parent selection are upright.

Plants of the new Poinsettia can be compared to plants of the male parent selection. Plants of the new Poinsettia differ primarily from plants of the male parent selection in the following characteristics:

1. Plants of the new Poinsettia are larger than plants of the male parent selection.
2. Roots of plants of the new Poinsettia are stronger than roots of plants of the male parent selection.

Plants of the new Poinsettia can be compared to plants of *Euphorbia pulcherrima* Willd. 'BKPONTW', disclosed in U.S. Plant Pat. No. 22,959. In side-by-side comparisons conducted in De Kwakel, The Netherlands, plants of the new Poinsettia differed primarily from plants of 'BKPONTW' in the following characteristics:

1. Plants of the new Poinsettia were larger than plants of 'BKPONTW'.
2. Flower bracts of plants of the new Poinsettia were smoother than flower bracts of plants of 'BKPONTW'.

3. Flower bracts of plants of the new Poinsettia were horizontal whereas flower bracts of plants of 'BKPONTW' were more upright.

BRIEF DESCRIPTION OF THE PHOTOGRAPHS

The accompanying photographs illustrate the overall appearance of the new Poinsettia plant showing the colors as true as it is reasonably possible to obtain in colored reproductions of this type. Colors in the photographs may differ slightly from the color values cited in the detailed botanical description which accurately describe the colors of the new Poinsettia plant.

The photograph on the first sheet comprises a side perspective view of a typical flowering plant of 'BKPONCH' grown in a container.

The photograph on the second sheet is a close-up view of a typical flowering plant of 'BKPONCH'.

DETAILED BOTANICAL DESCRIPTION

The aforementioned photographs and following observations and measurements describe plants grown during the autumn and early winter in 13-cm containers in a glass-covered greenhouse in Maasdijk, The Netherlands and under environmental conditions and cultural practices which approximate those generally used in commercial Poinsettia production. During the production of the plants, day temperatures averaged 20° C. and night temperatures averaged 18° C. Measurements and numerical values represent averages for typical flowering plants. Plants were pinched one time and were 3.5 months old when the photographs and the detailed description were taken. In the following description, color references are made to The Royal Horticultural Society Colour Chart, 2007 Edition, except where general terms of ordinary dictionary significance are used.

Botanical classification: *Euphorbia pulcherrima* Willd. 'BKPONCH'.

Parentage:

*Female, or seed, parent*.—Proprietary selection of *Euphorbia pulcherrima* Willd. identified as code number 204155-033, not patented.

*Male, or pollen, parent*.—Proprietary seedling selection of *Euphorbia pulcherrima* Willd. identified as code number 205265-001, not patented.

Propagation:

*Type*.—Terminal vegetative cuttings.

*Time to initiate roots, summer*.—About ten days at 22° C.

*Time to initiate roots, winter*.—About two weeks at 20° C.

*Time to produce a rooted young plant, summer*.—About 3.5 to four weeks at 20° C.

*Time to produce a rooted young plant, winter*.—About four weeks at 20° C.

*Root description*.—Medium in thickness, fibrous; white in color.

*Rooting habit*.—Moderately freely branching; medium density.

Plant description:

*Plant and growth habit*.—Upright plant habit; broad inverted triangle with rounded crown; large inflorescences positioned above the foliar plane; moderately vigorous growth habit.

*Plant height*.—About 34.5 cm.

*Plant diameter or spread*.—About 45.6 cm.

*Lateral branch description*.—Quantity: Freely branching habit, about ten lateral branches develop after pinching. Length: About 21.9 cm. Diameter: Thick, about 6 mm. Internode length: About 1.9 cm. Strength: Moderately strong. Texture: Smooth, glabrous. Angle: About 30° from vertical. Color: Close to 146A; towards the apex, tinged with close to 183A to 183B.

*Foliage description*.—Arrangement: Alternate, simple. Length: About 12.5 cm. Width: About 8.4 cm. Shape: Ovate. Apex: Apiculate. Base: Obtuse to short acuminate. Margin: Entire, angulate. Venation pattern: Pinnate. Texture, upper and lower surfaces: Glabrous; slightly rugose. Color: Developing leaves, upper surface: Darker than between N137D and 147A. Developing leaves, lower surface: Between 137B and N138B. Fully developed leaves, upper surface: Darker than between N137D and 147A; venation, close to 146A. Fully developed leaves, lower surface: Close to N138B; main vein, close to 148A and lateral veins, close to 147B. Petiole: Length: About 5.6 cm. Diameter: About 2.5 mm. Texture, upper and lower surfaces: Smooth, glabrous. Color, upper surface: Close to 183A to 183B. Color, lower surface: Close to 148B tinged with close to 177B.

Inflorescence description:

*Inflorescence type and habit*.—Inflorescences are compound corymbs of cyathia with bright red-colored flower bracts subtending the cyathia; one inflorescence per lateral branch with inflorescences positioned above and beyond the foliar plane.

*Fragrance*.—None detected.

*Natural flowering season*.—Plants flower naturally during the winter under long nyctoperiod conditions; inflorescence initiation and development can be induced under artificial long nyctoperiod conditions; early flowering habit, response time is about seven to eight weeks.

*Post-production longevity*.—Excellent post-production longevity; plants of the new Poinsettia maintain good substance and bract color for about six weeks under interior conditions.

*Inflorescence size*.—Diameter: About 26 cm. Height (depth): About 4 cm.

*Flower bracts*.—Quantity per inflorescence: About 17. Length: About 12.3 cm. Width: About 8.2 cm. Shape: Ovate. Apex: Apiculate. Base: Short acuminate. Margin: Entire. Venation: Pinnate. Aspect: Mostly horizontal to slightly drooping. Texture, upper surface: Glabrous; slightly rugose. Color: Developing bracts, upper surface: Close to 53A. Developing bracts, lower surface: Close to 46A. Transitional bracts, upper surface: Close to 46A. Transitional bracts, lower surface: Close to 46A to 46B. Fully developed bracts, upper surface: Close to 46A; color becoming closer to 53A with development. Fully developed bracts, lower surface: Close to 46A to 46B; color becoming closer to 53B to 53C with development. Bract petiole: Length: About 2.1 cm. Diameter: About 2 mm. Texture, upper and lower surfaces: Smooth, glabrous. Color, upper surface: Between 53A and 187C. Color, lower surface: Close to 46A.

*Cyathia*.—Quantity per corymb: About 15. Length: About 1.3 cm. Width: About 7 mm. Shape: Ovate. Color, immature and mature: Inner surface: Close to 143C; towards the apex, tinged with close to 53D. Outer surface: Close to 143B; towards the apex, tinged with close to 45A to 45B. Nectaries: Quantity per cyathium: About two. Length: About 3 mm. Diameter: About 3 mm. Color, immature: Inner surface: Close to 41B. Outer surface: Close to 154B. Color, mature: Inner surface: Close to 43A. Outer surface: Close to 21D.

*Peduncles*.—Length: About 7 mm. Diameter: About 3 mm. Strength: Moderately strong. Texture: Smooth, glabrous. Angle: Erect to about 40° from vertical. Color: Close to 146A.

*Reproductive organs*.—Stamens: Quantity per cyathium: About three. Filament length: About 4 mm. Filament color: Close to 46A. Anther shape: Club-shaped. Anther length: About 1 mm. Anther color: Close to 46A. Amount of pollen: Scarce to moderate. Pollen color: Close to 7A. Pistils: Quantity per cyathium: One. Pistil length: About 4 mm. Style length: About 3 mm. Style color: Close to 46A. Stigma shape: Flattened club-shaped. Stigma color: Close to 187A. Ovary color: Close to 143B. Seeds and fruits: Seed and fruit production has not been observed on plants of the new Poinsettia.

Disease & pest resistance: Plants of the new Poinsettia have not been shown to be resistant to pathogens and pests common to Poinsettia plants.

Temperature tolerance: Plants of the new Poinsettia have been observed to tolerate temperatures ranging from about 8° C. to about 35° C.

It is claimed:

1. A new and distinct Poinsettia plant named 'BKPONCH' as illustrated and described.

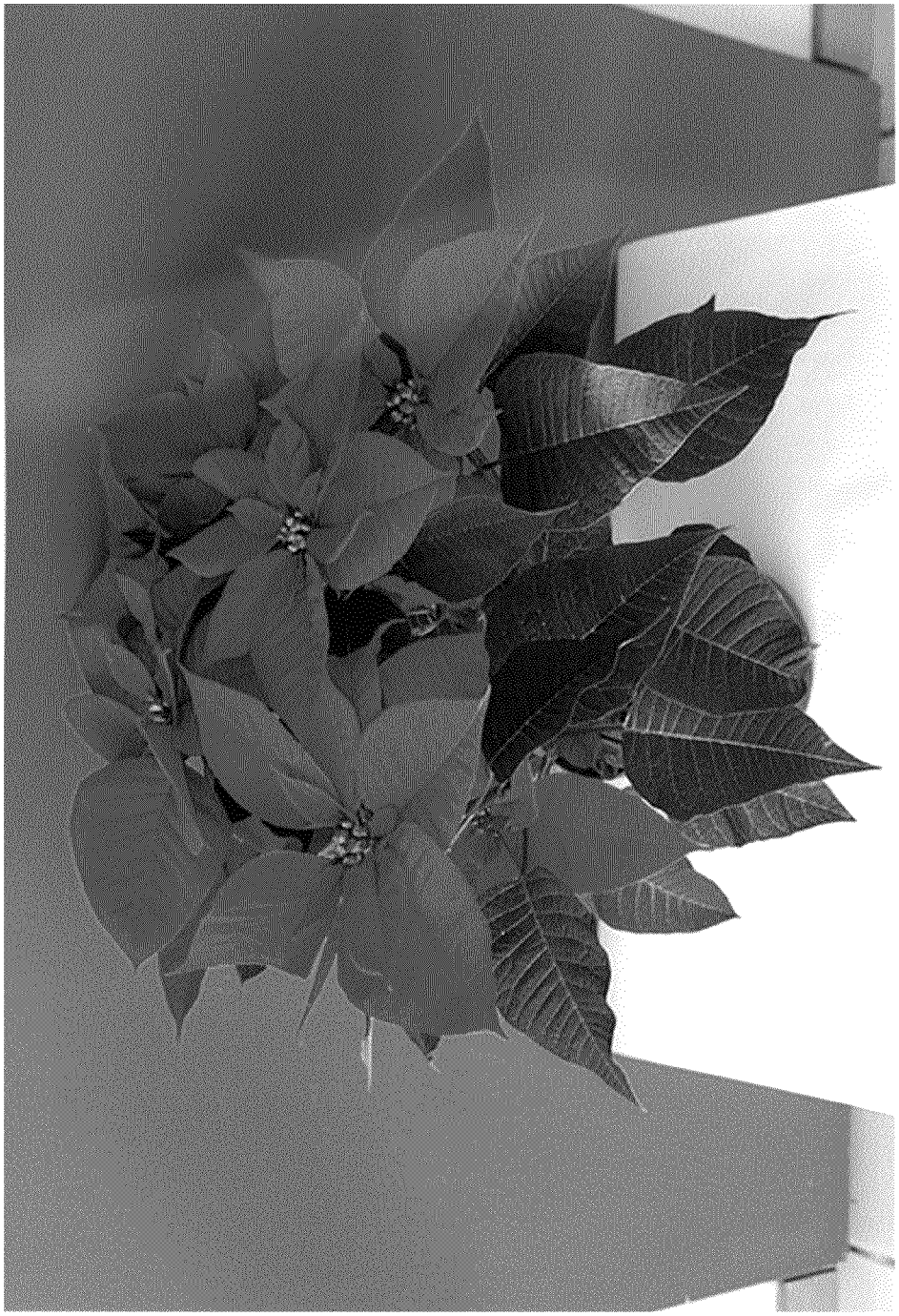

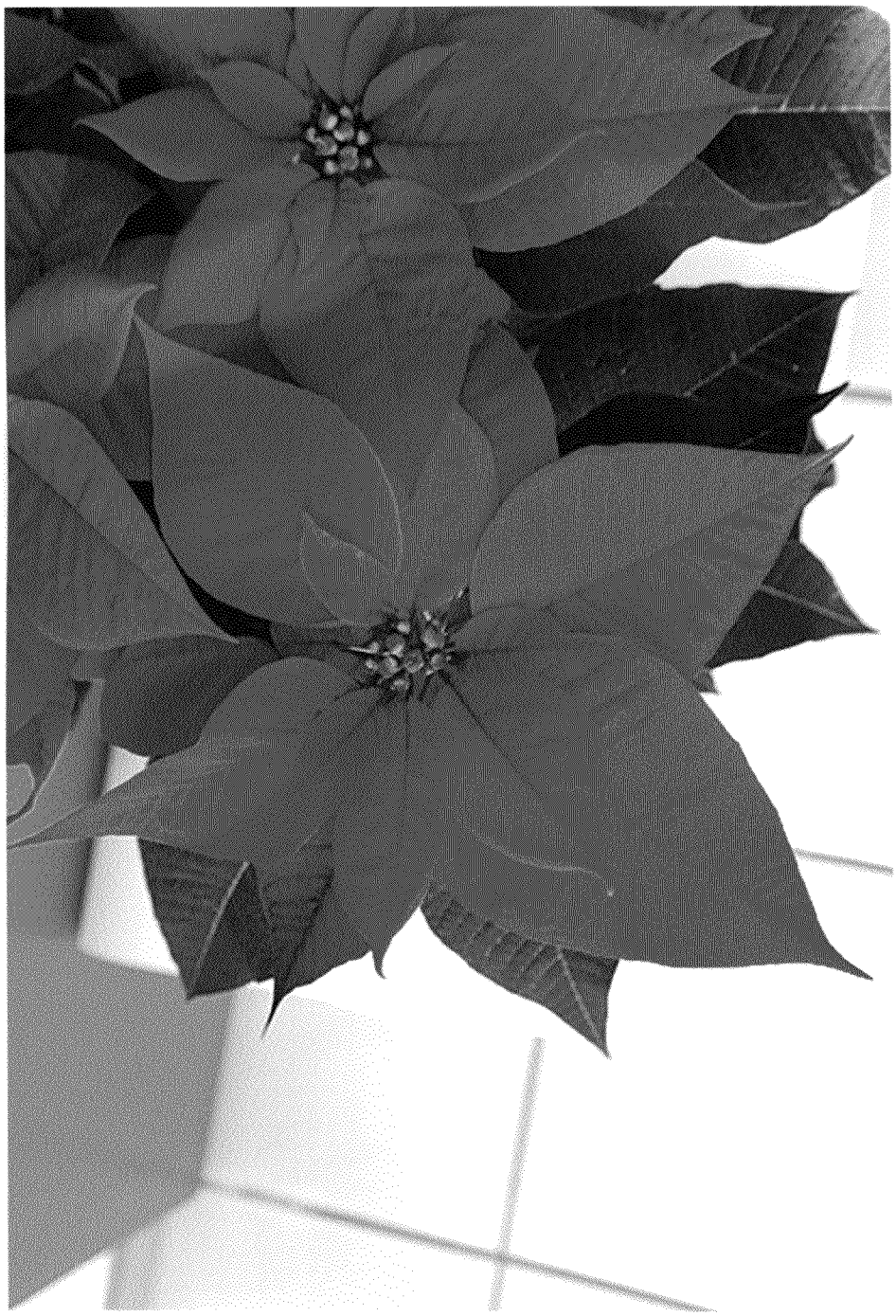

* * * * *